United States Patent [19]

Poduslo et al.

[11] Patent Number: 5,260,308
[45] Date of Patent: Nov. 9, 1993

[54] METHOD TO INCREASE PERMEABILITY OF THE BLOOD-NERVE/BRAIN BARRIERS TO PROTEINS

[75] Inventors: Joseph F. Poduslo; Geoffrey L. Curran, both of Rochester, Minn.

[73] Assignee: Mayo Foundation for Medical Education and Research, Rochester, Minn.

[21] Appl. No.: 788,497

[22] Filed: Nov. 6, 1991

[51] Int. Cl.$^5$ .................. C07K 3/08; A61K 37/02; A61K 37/26; A61K 37/04
[52] U.S. Cl. ...................... 514/21; 530/363; 530/387.1; 530/388.1; 530/388.24; 530/303; 530/359; 530/345; 514/8
[58] Field of Search .............. 514/21, 8; 530/363, 530/303, 345, 359, 363, 387.1, 388.1, 388.24

[56] References Cited

U.S. PATENT DOCUMENTS 3,903,262 9/1975 Pappenhagen et al. .
4,683,730 9/1989 Karpas .

FOREIGN PATENT DOCUMENTS 618555 8/1987 Australia .

OTHER PUBLICATIONS

J. Barnett et al., "Human Nerve Growth Factor Obtained from a Baculovirus Expression System Has Potent in Vitro and in Vivo Neurotrophic Activity", *Exp. Neurol.*, 110:11 (1990).
D. Baskin et al., "Insulin in the Brain", *Ann. Rev. Physiol.*, 49, 335 (1987).
D. Baskin et al., "Insulin and Insulin-Like Growth Factors in the CNS", *Trends in Neurosciences*, 11, 107 (1988).
S. Berkman et al., "Clinical Uses of Intravenous Immunoglobulins", *Ann. Int. Med.*, 112:278 (1990).
M. Brownlee et al., "Trapped Immunoglobins on Peripheral Nerve Myelin from Patients with Diabetes Mellitus", *Diabetes*, 35:999 (1986).
D. Cook et al., "High-dose Intravenous Immunoglobulin in the Treatment of Demyelinating Neuropathy Associated with Monoclonal Gammopathy", *Neurology*, 40:212 (1990).
L. Curtiss et al., "A Novel Method for Generating Region-Specific Monoclonal Antibodies to Modified Proteins", *J. Clin. Invest.*, 72:1427 (Oct. 1983).
W. Fischer et al., "Amelioration of Cholinergic Neuron Atrophy and Spatial Memory Impairment in Aged Rats for Nerve Growth Factor", *Nature*, 329:65 (1987).
A. Karpas et al., "Effects of Passive Immunization in Patients with the Acquired Immunodeficiency Syndrome-Related Complex and Acquired Immunodeficiency Syndrome", *PNAS USA*, 85:9234 (1988).
A. LeBlanc et al., "Regulation of Apolipoprotein E Gene Expression After Injury of the Rat Sciatic Nerve", *J. Neuroscience Res.*, 25:162 (1990).
P. Lipsky et al., "Intravenous Immunoglobulin. Prevention and Treatment of Disease", in *JAMA*, 264:3189 (1990).
J. Poduslo, "Glycoprotein Molecular-Weight Estimation Using Sodium Dodecyl Sulfate-Pore Gradient Electrophoresis: Comparison of Tris-Glycine and Tris-Borate-EDTA Buffer Systems", *Anal. Biochem.*, 114, 131 (1981).
J. Poduslo et al., "Altered Blood-Nerve Barrier in Experimental Lead Neuropathy Assessed by Changes in Endoneurial Albumin Concentration", *J. Neurosci.*, 2, 1507 (1982).
J. Poduslo et al., "Mammalian Endoneurial Fluid: Collection and Protein Analysis from Normal and Crushed Nerves", *Brain Res.*, 332, 91 (1985).

(List continued on next page.)

*Primary Examiner*—Michael G. Wityshyn
*Assistant Examiner*—Choon P. Koh
*Attorney, Agent, or Firm*—Merchant, Gould, Smith, Edell, Welter & Schmidt

[57] ABSTRACT

A method is provided to enhance the permeability of the blood-nerve barrier or the blood-brain barrier to neuroactive proteins, comprising glycating said proteins prior to bringing them into contact with said barriers.

18 Claims, 1 Drawing Sheet

OTHER PUBLICATIONS

J. Poduslo et al., "Increase in Albumin, IgG, and IgM Blood-Nerve Barrier Indices in Human Diabetic Neuropathy", *PNAS USA*, 85:4879 (1988).

E. Rechthand et al., "Regulation of the Microenvironment of Peripheral Nerve: Role of the Blood-Nerve Barrier", *Progress in Neurobiology*, 28:303 (1987).

M. Schwartz et al., "Kinetics and Specificity of Insulin Uptake from Plasma into Cerebrospinal Fluid", *Am. J. Physiol.*, 259:E378 (1990).

N. Shaklai et al., "Nonenzymatic Glycosylation of Human Serum Albumin Alters Its Conformation and Function", *J. Biol. Chem.*, 259:3812 (1984).

P. Smith et al., "Measurement of Protein Using Bicinchoninic Acid", *Anal. Biochem.*, 150, 76 (1985).

J. Tarsio et al., "Nonenzymatic Glycation of Fibronectin and Alterations in the Molecular Association of Cell Matrix and Basement Membrane Components in Diabetes Mellitus", *Diabetes*, 34, 477 (1985).

J. Tarsio et al., "Decreased Interaction of Fibronectin, Type IV Collagen, and Heparin Due to Nonenzymatic Glycation. Implications for Diabetes Mellitus", *Biochemistry*, 26, 1014 (1987).

P. Van Doorn et al., "On the Mechanism of High-Dose Intravenous Immunoglobulin Treatment of Patients with Chronic Inflammatory Demyelinating Polyneuropathy", *J. Neuroimmunol.*, 29:57 (1990).

A. Weerasuriya et al., "Blood-Nerve Transfer of Albumin and Its Implications for the Endoneurial Microenvironment", *Brain Res.*, 494, 114 (1989).

Patel et al., Diabetologia, (1991), 34:78-80.

Day et al., The J. of Biol. Chem., vol. 254, pp. 9394-9400, (1979).

METHOD TO INCREASE PERMEABILITY OF THE BLOOD-NERVE/BRAIN BARRIERS TO PROTEINS

BACKGROUND OF THE INVENTION

This invention was made with the support of the National Institutes of Health under grant number NS14304-P4. The U.S. Government has rights in the invention.

The interstitial connective tissue in the peripheral nerve that separates the individual nerve fibers of a vertebrate is referred to as the endoneurium, and can be visualized as an insulative medium in which conductive wires are embedded. Blood vessels in the endoneurium of peripheral nerves are comparable to those of the central nervous system and are lined by a continuous endothelium, made up of capillary endothelial cells, with intercellular tight junctions of high electrical resistance (100 ohm/cm$^2$). Together with the perineurium, a connective tissue sheath immediately surrounding the fascicles of nerve fibers, the vessels form a blood-nerve barrier (BNB) to regulate the micro-environment of the endoneurium of the nerve. The blood-cerebrospinal fluid barrier and the blood brain barrier (collectively the "BBB") are also associated with the tight junctions which adjoin adjacent capillary endothelial cells within the brain and spinal cord, to regulate this microenvironment as well.

The BNB and BBB are effective barriers to both endogenous and exogenously-administered blood components, including proteins and other large macromolecules, as well as to ions and water-soluble non-electrolytes. This protects the brain or endoneurial microenvironment from rapid changes in the composition of the blood or of the extra neural spaces. Also, alterations in BBB or BNB integrity are implicated in a number of common peripheral nerve disorders, such as those caused by diabetes mellitus, toxins, infection and autoimmune disorders.

However, the ability of the BNB and BBB to protect the nervous system from exogenous substances has impeded the development of both diagnostic assays and therapies for diabetic neuropathy and other neural disorders. Thus, a continuing need exists for methods to increase the permeability of the BNB or the BBB to bioactive substances, particularly to bioactive proteins.

SUMMARY OF THE INVENTION

The present invention provides a general method for enhancing the permeability of the blood-nerve barrier (BNB) or the blood-brain barrier (BBB) of a vertebrate such as a mammal, to a selected bioactive protein by pre-glycating the protein. The method comprises contacting cells constituting the BNB or the BBB of the vertebrate, either in vitro or in vivo, with the selected bioactive protein in a suitable physiological fluid, wherein said bioactive protein is glycated so that an effective amount of said bioactive protein is introduced into the nervous system. As used herein, the term "glycated" refers to a protein which as been nonenzymatically glucosylated, by reaction with glucose in a suitable media, or with another non-toxic sugar that at least equivalently facilitates the transport of the protein across the BNB or BBB.

Although the preferred embodiments of the present invention involve the treatment of neural diseases and disorders by the administration of glycated bioactive proteins, including recombinant polypeptides, to humans thus afflicted, the present method can also be practiced in vitro, on isolated neural tissue, in order to diagnose neuronal disorders, e.g., by measuring the integrity of the BNB or the BBB. Furthermore, the glycated bioactive protein can act effectively as a carrier for a second bioactive compound. For example, glycated albumin can function as a carrier for a wide variety of bioactive substances such as fatty acids, thyroxine, typtophan and the like. Also, a glycated antibody can be used to complex and transport a neuroactive antigen across the BNB or BBB, and a glycated neuroreceptor can transport a neurotransmitter or other neuropharmaceutical agent across these barriers.

The present invention is based on our finding that the microvascular permeability of glycated albumin across the blood nerve barrier is substantially increased compared to that exhibited by non-glycated albumin. Furthermore, the longer the duration of glycation, the greater is the increase in the permeability In addition, the glycated albumin isolated from patients with diabetic polyneuropathy also demonstrates an increased permeability across the rat BNB. Therefore, it is believed that the preferential transport of glycated proteins across the BNB accounts for the quantitative increases in the concentration of plasma proteins that we have observed in the fascicular biopsies of diabetic neuropathy patients. See J. F. Poduslo et al., *PNAS USA*, 85, 4879 (1988). Evidence that this phenomenon is general to glycated macromolecules is provided by the observation by M. Brownlee et al., in *Diabetes*, 35, 999 (1986) that increased levels of IgG and IgM occur in the fascicular biopsies of diabetic patients. They demonstrated a 14-fold increase of trapped IgM and a 4-fold increase in trapped IgG in peripheral nerve myelin. We believe that this trapped immunoglobulin was glycated and preferentially transported across the BNB. Such trapping on myelin may contribute to the development of peripheral nerve damage in diabetic neuropathy patients via classical immunological mechanisms. However, as discussed hereinbelow, the facilitated transport of administered immunoglobulins such as polyvalent intravenous immunoglobulin can have an ameliorating effect on certain neurological disorders.

With respect to transport across the mammalian BBB, we have also found that a glycated form of neuronal growth factor (NGF) achieves a seven-fold increase in delivery into rat brain hippocampus compared to controls treated with the non-glycated polypeptide. NGF has been reported to have beneficial effects on age-associated deficits and behaviors dependant on the septohippocampal circuit by W. Fischer et al., *Nature*, 329, 65 (1987).

DETAILED DESCRIPTION OF THE INVENTION

Bioactive Proteins

Figure 1:
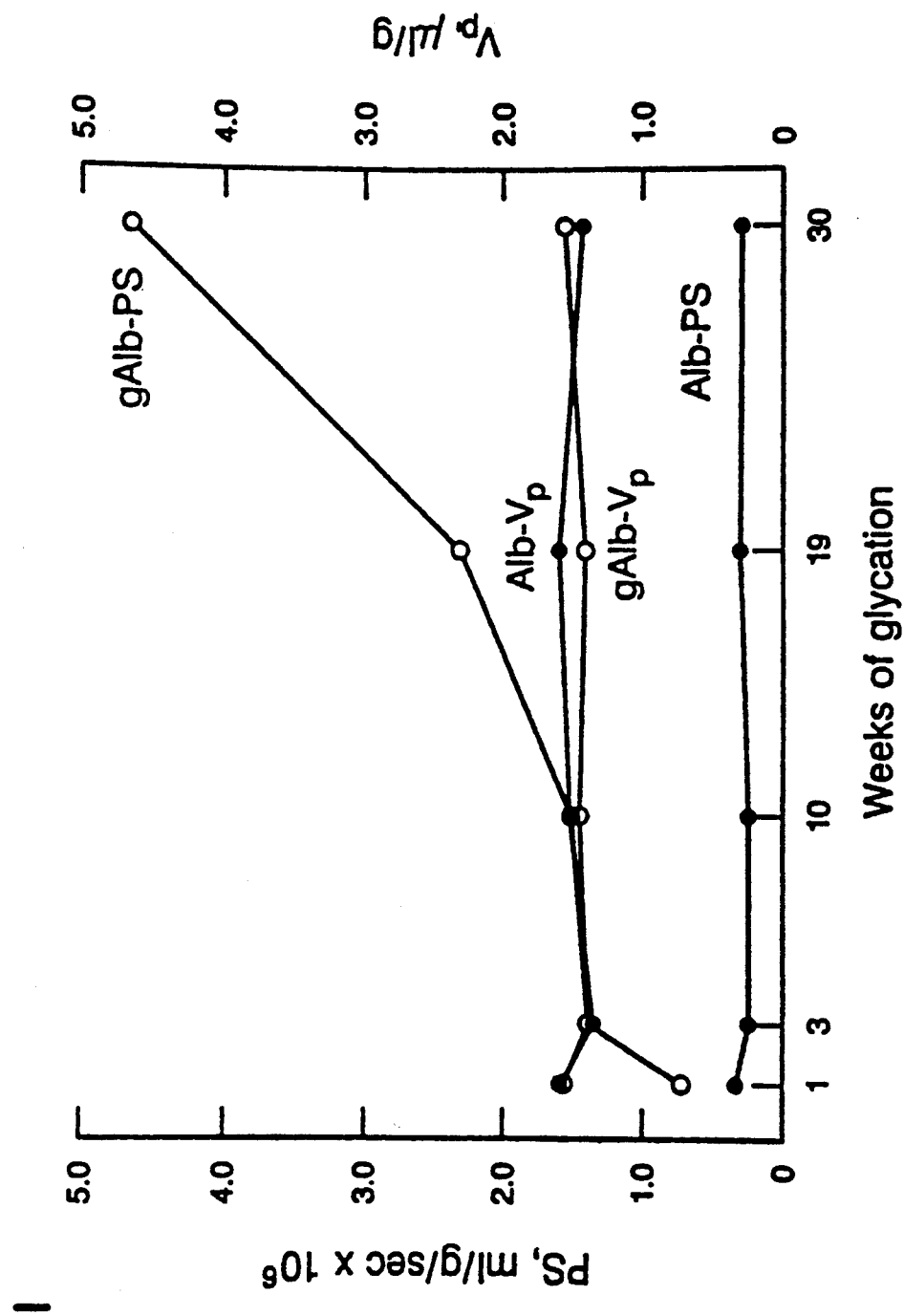
FIG. 1 is a graphical depiction of the correlation of increased gALB-PS with duration of glycation. No change is observed in the ALB PS or the ALB-$V_p$, and gALB-$V_p$.

In accord with the invention, the proteins which can be introduced into nervous system, i.e., into the endoneurial or brain microenvironment, in accord with the present method include any bioactive protein or protein mixture which can be purified and nonenzymatically glucosylated or "glycated" (chemically linked to a glucose without the involvement of enzymes), so that its ability to cross the BNB or the BBB is substantially enhanced over the nonglycated form of the protein. The term "substantially enhanced" or "enhanced" is to be understood in the context of the increases in permeability across the BNB or the BBB observed for nonenzymatically glycated albumin and NGF over that observed for the non-glycated forms, i.e., and at least about 5–20-fold increase. As used herein with respect to the glycated proteins useful in the present method, the term "bioactive" means that the glycated protein (a) exerts a beneficial therapeutic effect upon introduction into the nervous system, e.g., by stimulating nerve growth or activity, neuralizing a pathogen, and the like; (b) the glycated protein can serve as a useful biological marker, e.g., to assess the viability of the BNB or the BBB, or to serve as a probe for the presence an analyte suspected to be present in the endoneurial microenvironment; or (c) the glycated protein, e.g., glycated albumin, a glycated neuroreceptor protein or a glycated antibody can serve as a carrier for another bioactive agent; to transport it across the BNB or BBB. Thus, while a glycated protein may not exert a beneficial effect on the nervous system, it can be useful to assess the permeability of the components of the BNB or BBB. Although, the therapeutic embodiment of the present invention will involve administering an effective amount of the glycated protein to a mammal in vivo, analytical and/or diagnostic uses of the present method can be carried out in vitro, on isolated tissues or tissue sections. Thus, for in vitro use, the physiological fluid can be an intravenous fluid such as normal saline, artificial CSF or PBS, while for in vivo use, the physiological fluid in which the BNB and the protein are contacted is blood, endoneurial fluid, CSF and the like.

Thus, the present method can employ essentially any desired protein, including those having lower molecular weights, e.g., 5000 daltons or less (as used herein, the term protein shall include those compounds which might be referred to as polypeptides because of their molecular weight), as well as those having molecular weights of several hundred thousand or more. Representative classes of proteins include protamines, mucoproteins, glycoproteins, globulins, albumins, phosphoproteins, histones, lipoproteins, chromoproteins, and nucleoproteins. Useful blood plasma proteins include laminin, albumin, immunoglobulin, transferrin, low-density lipoproteins, fibrinogen, fibronectin, plasminogen, plasmin and mixtures thereof. For example, unreduced, nonenzymatically-glycated total serum proteins can be used as the antigenic preparation.

Preferred proteins for glycation and use in the present method include immune serum globulin, or immunoglobulin and bioactive fractions and subunits derived therefrom such as IgG, IgM or IgA and the F(ab')$_2$ and F(ab) fragments thereof. For example, administration of normal polyspecific immunoglobulins ("IVIg" or "IVIG") (0.4 g/kg) has been found to ameliorate the symptoms of chronic inflammatory demyelinating polyneuropathy or "Guillain Barre syndrome" (GBS). Apparently, the IVIg antibodies inhibit reaction between the patient's autoantibodies that attack the sciatic nerve. P. A. Van Doorn et al., *J. Neuroimmunol.*, 29, 57 (1990). Other treatment regimens are given in D. Cook et al., *Neurology*, 40, 212 (1990).

Likewise, Karpas (U.S. Pat. No. 4,863,730) discloses method to treat a viral immunodeficiency disease, such as HIV, by processing plasma from symptom-free, infected donors to yield a preparation having a high titer of antibodies possessing virus-neutralizing properties. The preparation is then intravenously infused into an infected patient and repeated as necessary. See also A. Karpas et al., *PNAS USA*, 85, 9234 (1988). L. M. Cummins et al., Australian Patent No. 618,555 discloses an IgG preparation which exhibits a high anti-HIV p24 antibody titer and a T$_4$ lymphocyte count of at least 400/ml of blood, which is also useful for treating AIDS patients, ARC patients, or other HIV-infected patients. The present method can deliver such IgG preparations to the nervous system and ameliorate the encephalitis and other HIV-associated neuropathies. Other viral infections which may be amenable to treatment by the present method include HCMV, EBV, echovirus meningoencephalitis, myasthenia gravis and amyotrophic lateral sclerosis.

The use of intravenous immunoglobulin preparations, or of monoclonal antibodies corresponding to the active antibody component thereof, is discussed by P. E. Lipsky et al., in *JAMA*, 264, 3189 (1990) and by S. A. Berkman et al., *Ann. Int. Med.*, 112, 279 (1990). A number of IVIG preparations are commercially-available, including Gammagard ® (Baxter Healthcare Corp.), Gaimmun ®N (Cutter) and Sandoglobulin ® (Sandoz AG).

Furthermore, monoclonal and polyclonal antibodies can now be raised to virtually any protein, peptide, lipid, carbohydrate or nucleic acid. Glycation of antibodies can allow efficient delivery of the antibody to the nervous system. In turn, the glycated antibody can be used as a vehicle to bind to its corresponding antigen and thus, to transport it into the nervous system.

Other neuroactive proteins that may be potentiated using the present method include the group of proteins that are generally referred to nerve growth factors. These include nerve growth factor itself (NGF), Brain-Derived neurotrophic factor (BDNF), neutrotrophin-3 (NT-3) and ciliary neurotropic factor (CNTF). NGF (total dose infused i.v.=1ug) has been reported to ameliorate cholinergic neuron atrophy and spatial memory impairment in aged rats by W. Fischer et al., *Nature*, 329, 65 (1987). Recombinant human beta NGF has been produced which has potent in vitro and in vivo neurotropic activity. See J. Barrett et al., *Exp. Neurol.*, 110, 11 (1990). Therefore, glycation and exogenous administration of neuronal growth factors may be helpful to treat pathological disorders involving degenerative processes, including Alzheimer's disease or diabetic associated polyneuropathy.

The present method can also be used to deliver insulin to the nervous system. Since it has been demonstrated that there is a widespread distribution of insulin receptors in brain, insulin is likely to have important functions in the central nervous system. It is suggested that insulin may function as a neurotrophic factor and neuromodulator by D. G. Baskin et al., *Trends Neurol.*, 11, 107 (1988) and D. G. Baskin et al., *Ann. Rev. Physiol.*, 49, 335 (1987). Brain insulin receptors have been evaluated by in vitro autoradiography and immunohistochemistry and appear heterogeneous. High concentrations of insulin receptors are found in discrete brain nuclei and suggest that insulin action may be targeted to specific neural cell types. Since injection of insulin to the hypothalamus or ventricular CSF produces satiety and weight loss, insulin may act as a central adiposity signal by binding to the hypothalamic and other brain insulin receptors. In addition, M. W. Schwartz et al., *Am. J. Physiol.*, 259, E378-E383 (1990) found significant elevations of CSF insulin levels that are consistent with the hypothesis that insulin uptake into the CSF occurs by a mechanism that is specific for insulin and is probably receptor mediated. Because of the metabolic and growth-promoting functions of insulin, it may also play a critical role in nerve tissue differentiation and function, as well as in nerve regeneration.

The present method can also be used to enhance and to evaluate the transport of apolipoprotein E across the BNB, since exchange of this protein from the plasma to the nerve, or vice-versa, is believed to be involved in cholesterol transport. Various apolipoproteins, including A-1, A-11 and B are available from Sigma Chem. Co.

The present invention is exemplified primarily by reference to the BNB transport of glycated albumin. Another aspect of the present invention involves the use of the known binding affinity of albumins such as human serum albumin (HSA) for a wide variety of agents to transport neuropharmaceutical agents into the nervous system. For example, albumin associates strongly with fatty acids, phospholipids, lysolecithin, thyroxine, tryptophan, cortisol, testosterone, bilirubin, salicylate, sulfisoxazole, penicillin, phenylbutazone, diphenyl hydantoin, acetylsalicylate, diazepam, amitriptyline, imipramine, phenytoin, methadone, and the like.

Another class of proteins that can be glycated and used as a carrier to transport their "partner" neuropharmaceutical agents into the nervous system, are the neuro receptors or soluble peptides isolated therefrom. These include receptors for neurotransmitters (epinephrine, norepinephrine, dopamine, serotonin, GABA, glycine, glutamate, and the like); neuropeptides ($\beta$-endorphin, enkephalins, somatostatin, neurotensin, angiotensin vasoactive intestinal peptide, and the like); and neurohormones (luteinizing hormone releasing hormone, thyrotrophin-releasing hormone, substance P, and the like).

Nonenzymatic Glycation

General methods for the production of nonenzymatically-glycated proteins from various proteins have been developed, i.e., by J. F. Tarsio et al., *Diabetes*, 34, 477 (1985), and in *Biochemistry*, 26, 1014 (1987). The mechanism of this reaction involves the formation of a Schiff base between glucose and the N-terminal amino group of a protein or the epsilon-amino group of at least one hydroxyllysine or lysine in the protein, with subsequent formation of a stable ketoamino linkage via Amadori rearrangement. In a typical procedure, a mixture of the protein or proteins in a buffered physiological salt solution such as phosphate-buffered saline (PBS) is incubated with excess D-glucose for 10-20 days under ambient conditions, preferably in the present of an effective amount of protease inhibitors and preservatives. Other sugars are known to be more effective glycating agents, and may increase the efficiency of the protein glycation. The biological activity of these proteins can be maintained by modifying the conditions of the glycation reaction, by changes in time, pH, tonicity, substrate, substrate concentration and the like.

The glycated protein can be isolated by dialysis, or boronate affinity chromatography, resuspended in a physiological salt solution for the desired concentration, and an effective amount thereof administered to a mammal, e.g., to a human patient, or to a target tissue in vitro. The extent of nonenzymatic glycation of the in vitro glycated proteins and their corresponding controls is determined by labeling the glucose moieties on the proteins, i.e., by reductive tritiation with $NaB^3H_4$. The protein is then hydrolyzed and the labelled, glycated amino acids separated on boronate columns. The level of nonenzymatic glycation of each in vitro glycated protein is then expressed as cpm of glycated amino acids per mg bf protein. Usually glycation is increased at least about 3-20-fold in the glycated proteins, as compared to the controls.

Administration

The nonenzymatically glycated bioactive proteins useful in the present method will primarily be formulated for parenteral, i.e., for intravenous or intraperitoneal administration. Thus, the present therapeutic method will employ pharmaceutical compositions comprising a solution or dispersion, in a pharmaceutically acceptable aqueous carrier adapted for intravenous administration, of an intravenously injectable or infusible glycated protein or protein mixture. The glycated protein is substantially pure, in that it is substantially free of nonglycated proteins and of any non-proteinaceous reactants or products of the glycation reactions. The glycated protein is present in these solutions in any useful concentration, either suitable for immediate I.V. administration or after dilution, e.g., with isotonic saline solution, to acceptable levels, e.g., about 0.5-20 percent solution, preferably about 1-15 percent. These solutions are sterile and free of particulate matter. A variety of aqueous solvents for the protein can be employed, e.g., water, buffered water, 0.4 percent saline, 0.3 molar glycine, and the like.

In its therapeutic method aspect, this invention preferably relates to the intravenous administration, usually to humans, of a pharmaceutical composition as defined above. The composition is administered in a conventional manner, e.g., in an amount which provides adequate therapeutic amounts of the glycated protein. For example, for a 10-20 wt-% glycated immunoglobulin (antibody) solution, about 1-25 ml. is the customary single dose. Administration of subsequent dosages is usually within 1-3 weeks, depending upon the severity of the illness and the time of exposure thereto. The effective amounts of other glycated proteins can be determined by extrapolating from the amounts of non-glycated bioactive proteins employed to achieve beneficial results in humans, and in the animal models discussed herein. As is recognized by the art, the rat has historically been one of the most successful animal models for studying the mammalian peripheral nervous system. In fact, early studies on measuring permeability across the BNB have used these vertebrate animals.

The invention will be further described by reference to the following detailed examples wherein twenty-four week old Sprague Dawley male rats (460-500 grams) were obtained from Biolab (St. Paul, Minn.) and used to determine the PS and $V_p$ measurements. The animals were kept for a minimum of three days under standard housing conditions and feeding schedules prior to being used for experiments. Reagents were obtained from the following sources: Glyc-Affin GHb from Isolab, Inc., (Akron, Ohio); CM-Affi-Gel Blue from BioRad Laboratories (Richmond, Cal.); carrier-free $Na^{125}I$ and $Na^{131}I$ from Amersham (Arlington Heights, Ill.).

EXAMPLE 1

Isolation of Human Albumin

CM-Affi-Gel Blue was used to isolated albumin from normal human plasma according to the manufacturer's instructions. The albumin fraction was extensively dialyzed against phosphate buffered saline (PBS), pH 7.4. Aliquots of normal plasma albumin (1 mg) were stored at −70° C. Protein concentrations were determined by the BCA protein assay procedure of P. K. Smith et al., *Anal. Biochem.*, 150, 76 (1985), using the Pierce assay kit (Rockford, Ill.). The purity of the human albumin was monitored by SDS-pore gradient electrophoresis (SDS-PGE) on a linear gradient with a gel concentration of 10–20% T and 1% C according to the procedure of J. F. Poduslo, *Anal. Biochem.*, 114, 131 (1981). Albumin was solubilized and electrophoresed as described by J. F. Poduslo et al., *Brain Res.*, 332, 91 (1985). After electrophoresis, gels were fixed in methanol/water/acidic acid (45/45/10; v/v/v) and stained with Coomaasie blue or processed for direct autoradiography by exposure to Kodak X-OMAT AR film.

EXAMPLE 2

Preparation of Glycated Albumin

Human albumin was glycated for a period of 1, 3, 10, 19, and 30 weeks utilizing a modification of the method as described by N. Shaklai et al., *Biol. Chem.*, 259, 3812 (1984), in which 25 mg of the human albumin preparation was incubated with 500 mM D-glucose at 37° C. under sterile conditions. At the end of each time period, the mixture was dialyzed for three days against multiple changes of phosphate buffered saline to ensure complete removal of unbound glucose. In some experiments 25 mg of human albumin was incubated with 0.5–5 Ci of $D[U-^{14}C]$ glucose (286 mCi/mmol; Amersham) for varying time periods.

EXAMPLE 3

Boronate Affinity Chromatography

Glycated human albumin was separated from the nonglycated species by boronate affinity chromatography on prepacked Glyc-Affin GHb columns (1 ml). The column was initially equilibrated with 0.25M ammonium acetate 0.01M $MgCl_2$, pH 8.4 which was used both as a sample solvent and to elute the nonbound albumin fraction. Glycated human albumin was eluted with 0.5M sorbitol in 0.1M Tris HCl, pH 8.5. The nonbound albumin fraction and the bound glycated albumin fractions were monitored by absorbance at 280 nm. Samples of each were pooled and dialyzed against PBS for three days with multiple changes.

Aliquots of both the nonbound ALB and the gALB bound to the boronate affinity column (1 mg) were labelled with $^{125}I$ and $^{131}I$ using the chloramine T method of J. F. Poduslo et al., *PNAS USA*, 85, 4879 (1988). The free radioactive iodide was separated from the radiolabelled albumins by dialysis against 0.2M NaI. The purity of the radiolabelled albumins was determined by paper chromatography as described by J. F. Poduslo et al., *J. Neurosci.*, 2, 1507 (1982). The radioactive labeled-protein that stayed at the origin was always greater than 99%. Specific activities for the $^{125}I$ and $^{131}I$ ALB and gALB were about 1 mCi/mg and 2.5 mCi/mg, respectively.

The efficiency of the separation of the ALB and gALB by borate affinity chromatography was investigated using several approaches. Human serum albumin (25 mg) was incubated with 0.5–5 $\mu$Ci $D-[U-^{14}C]$ glucose for varying time periods. Albumin in the washed (unbound) and eluted (bound) fractions was determined by UV absorbance at 280 nm, and the extent of glycated albumin was determined by assessing total radioactivity using a Beckman LS5801 liquid scintillation counting system. The radioactivity representing gALB eluted as a second peak which corresponded to the protein absorbance. This indicates that glucose is covalently attached to the albumin and is eluted from the borate affinity column only after sorbitol treatment. The radioactivity in the unbound fraction represents remaining free $[^{14}C]$ glucose that was not completely removed by dialysis. Additional dialysis resulted in the removal of this radioactivity.

To further test the efficiency of the borate affinity column to separate ALB from gALB, samples were pooled from the non-bound and bound fractions of the borate column, subjected to radioiodination, and rechromatographed on boronate columns. The albumin species that previously bound to boronate columns remained bound to the boronate column after subsequent radioiodination and was eluted efficiently with sorbitol but not with citrate. In contrast, the non-bound species showed no binding to the boronate column and eluted in the void volume. This experiment indicates that the borate affinity chromatography approach was highly efficient in separating the glycated species from the non-glycated species, even after radioiodination.

EXAMPLE 4

SDS-Pore Gradient Electrophoresis in Tris-Borate-EDTA Buffer

The nonbound ALB and the gALB bound to boronate columns were evaluated by SDS-pore gradient electrophoresis under reducing and nonreducing conditions on a linear gradient with a gel concentration of 10–20% T and 1% C. Separation was not achieved with a standard Tris-glycine buffer system but rather was obtained with a Tris-borate-EDTA buffer as described by J. F. Poduslo, *Anal. Biochem.*, 114, 131 (1981). This separation is based on the ability of borate ions to react with neutral sugars converting them to a charge complex at alkaline pH. The formation of borate complexes with the carbohydrate moieties of glycated albumin would increase the net negative charge which would affect the SDS binding to the glycated protein resulting in a charge density that would alter its migration compared to the nonglycated species The purity of the albumins and also the extent of glycation of the glycated albumin fraction was assessed by both Coomaasie blue stain and direct autoradiography of the radioiodinated albumins after SDS-PGE.

After glycation for a period of three weeks, the gALB showed a higher apparent molecular weight after electrophoresis as determined by both Coomaasie blue staining and autoradiography of the radioiodinated species. Similar results were also obtained with a glycation time of one week which indicates that the gALB is free of significant amounts of native ALB.

EXAMPLE 5

Permeability Coefficient-Surface Area Product (PS) and Residual Endoneurial Plasma Volume ($V_p$) of the Blood Nerve Barrier for Albumin Glycated In Vitro The experimental procedures used to determine the PS and $V_p$ values of the ALB and gALB were in accord with A. Weerasuriya et al., *Brain Res.*, 494, 114 (1989). Briefly, the brachial vein and artery were catheterized in pentobarbital-anesthetized rats. A bolus of phosphate buffered saline containing $^{125}$I-ALB or $^{125}$I-gALB was rapidly injected into the brachial vein. Blood was sampled during the next 60 minutes from the brachial artery. Two minutes prior to the sacrifice of the animal the $^{131}$I-ALB or $^{131}$I-gALB was intravenously administered and served as a residual plasma volume indicator. Total ALB injected per rat was less than 160 μg. The $V_p$ and PS measurements were calculated as described previously and as recently reviewed by J. F. Poduslo in *Peripheral Neuropathy*, P. J. Dyck et al., eds., W. B. Saunders, Philadelphia (3rd ed. 1992).

Albumin was glycated for 1, 3, 10, 19, and 30 weeks. After each time period, gALB was separated from ALB by boronate affinity chromatography. The proteins were then radioiodinated with $^{125}$I and $^{131}$I, respectively, and the PS for both gALB and ALB were determined in normal rats. ALB, therefore, served as the control which had undergone the same incubation procedure with glucose for same time periods as did gALB.

As shown in FIG. 1, a progressive increase in the gALB-PS was observed with increased time of glycation. In contrast, no change was observed in the ALB-PS during the same incubation period. In addition, no changes were observed in either the ALB-$V_p$ or the gALB-$V_p$ during the duration of the experiment. A 2.2 fold increase was observed in the gALB-PS as compared to the ALB-PS at 1 week, a 5.9 fold increase at 3 weeks, a 6.2 fold increase at 10 weeks, a 7.7 fold increase at 19 weeks, and a 16.2 fold increase at 30 weeks (Table I). These increases were all highly significant as determined by the two-sample t-test (Table I). As expected, no significant changes were observed in $V_p$ of ALB and gALB. These studies, therefore, demonstrate a direct correlation between the increase of gALB-PS and the duration of glycation.

TABLE I

ALTERATIONS IN PS AND $V_p$ OF THE BLOOD-NERVE BARRIER FOR Alb AND gAlb WITH INCREASED DURATION OF GLYCATION

| Weeks of glycation | Alb | | gALB | | P | |
|---|---|---|---|---|---|---|
| | $V_p$, μl/g | PS ml/g/sec ×10$^6$ | $V_p$, μl/g | PS ml/g/sec ×10$^6$ | $V_p$ | PS |
| 1 | 1.582 ± 0.319 | 0.328 ± 0.053 | 1.557 ± 0.386 | 0.724 ± 0.063 | NS | <0.0001 |
| 3 | 1.349 ± 0.279 | 0.236 ± 0.056 | 1.391 ± 0.524 | 1.386 ± 0.128 | NS | <0.0001 |
| 10 | 1.516 ± 0.383 | 0.244 ± 0.057 | 1.446 ± 0.243 | 1.507 ± 0.492 | NS | 0.0002 |
| 19 | 1.596 ± 0.288 | 0.299 ± 0.043 | 1.409 ± 0.135 | 2.313 ± 0.835 | NS | 0.0003 |
| 30 | 1.430 ± 0.302 | 0.288 ± 0.042 | 1.560 ± 0.449 | 4.656 ± 1.117 | NS | <0.0001 | n = 8-12 nerves
x ± SD
P = two-sample t-test
NS = no significant (P >0.05)

EXAMPLE 6

PS and $V_p$ of the Blood Nerve Barrier for Albumin Glycated In Vivo in Diabetic Polyneuropathy Patients ALB and gALB were isolated from two patients with diabetic polyneuropathy, and their PS and $V_p$ were determined (Table II). Patient #1 had a fasting blood glucose of 494 mg/dL, 19.5% glycated hemoglobin, and 8.3% glycated albumin. The gALB-PS was increased approximately 1.8 fold in this patient with a highly significant p value (p<0.0001). Patient #2 had a fasting blood glucose of 314 md/dL, 16.0% glycated hemoglobin, and 35.4% glycated albumin. This patient had a 4.6 fold increase in the gALB-PS compared to the ALB-PS which was highly significant (p<0.0001). Patient #1 also showed a significant increase in the $V_p$ (p<0.005), whereas patient #2 showed no significant difference in the $V_p$ values. These experiments indicate that ALB glycated in vivo in patients with diabetic neuropathy also shows an increase in permeability across the blood nerve barrier of normal rats.

TABLE II

PS AND $V_p$ OF THE BLOOD-NERVE BARRIER FOR ALBUMIN AND GLYCATED ALBUMIN ISOLATED FROM PATIENTS WITH DIABETIC POLYNEUROPATHY

| | Pt 1 | Pt 2 |
|---|---|---|
| Fasting blood glucose, mg/dl | 494 | 314 |
| Glycated hemoglobin, % | 19.5 | 16.0 |
| Glycated albumin, % | 8.3 | 35.4 |

| | Alb | gAlb | P | Alb | gAlb | P |
|---|---|---|---|---|---|---|
| PS, ml/g/sec ×10$^6$ n = 12 | 0.38 ± 0.11 | 0.67 ± 0.12 | <0.0001 | 0.320 ± 0.12 | 1.47 ± 0.29 | <0.0001 |
| $V_p$ | 1.08 ± 0.19 | 1.73 ± 0.56 | <0.005 | 1.47 ± 0.31 | 1.53 ± 0.37 | NS |

TABLE II-continued

PS AND $V_p$ OF THE BLOOD-NERVE BARRIER
FOR ALBUMIN AND GLYCATED ALBUMIN ISOLATED
FROM PATIENTS WITH DIABETIC POLYNEUROPATHY

μl/g
n = 12

$\bar{x} \pm$ SD
P = two-sample t-test
NS = no significant (P >0.05)

Examples 1-6 demonstrate that the microvascular permeability to gALB across the blood nerve barrier of normal rats is significantly increased compared to the non-glycated protein. Furthermore, the longer the duration of glycation the greater is the increase in permeability. In addition, the glycated albumin isolated from patients with diabetic polyneuropathy also demonstrates an increased permeability across the blood nerve barrier. Specifically, after one week of glycation, the gALB-PS was 2.2 fold greater than the ALB-PS (0.724±0.063, S.D.×$10^{-6}$ vs.0.328±0.053, S.D.×$10^{-6}$ ml/g/s; P<0.0001) and increased with the time of glycation reaching a maximum value of 16.2 fold greater at 30 weeks (4.656±1.117, S.D.×$10^{-6}$ vs. 0.288±0.042, S.D.×$10^{-6}$ ml/g/s; p<0.0001). No change was observed in the residual endoneurial plasma volume ($V_p$). In addition, the PS of gALB isolated from patients with diabetic polyneuropathy was significantly increased (P<0.0001) compared to the PS for albumin isolated from the same patients.

It is believed that the increased permeability of glycated albumin and presumably other glycated serum components across the BNB, as well as the observed quantitative increase in albumin, IgG, and IgM in sural nerve biopsies from patients with diabetic polyneuropathy, can provide the basis for a general method to enhance the transport of bioactive proteins across the BNB, the BBB or both.

All of the patents, patent documents and publications cited herein are incorporated by reference herein.

The invention has been described with reference to various specific and preferred embodiments and techniques. However, it should be understood that many variations and modifications may be made while remaining within the spirit and scope of the invention.

What is claimed is:

1. A method for enhancing the permeability of the blood-nerve barrier (BNB) or the blood-brain barrier (BBB) of a mammal to a selected bioactive protein comprising contacting cells constituting the BNB or the BBB of the mammal with said selected bioactive protein in a suitable physiological fluid, wherein said bioactive protein is glycated so that an effective amount of said bioactive protein is introduced into the nervous system.

2. The method of claim 1 further comprising the step of glycating the selected bioactive protein in vitro prior to contacting the cells with said bioactive protein.

3. The method of claim 1 wherein said contacting is conducted in vitro on isolated neural tissue.

4. The method of claim 1 wherein said contacting is conducted in vivo by administering said glycated protein to said mammal.

5. The method of claim 4 wherein said mammal is a human.

6. The method of claim 5 wherein said glycated protein is administered to said human parenterally.

7. The method of claim 6 wherein the glycated protein is administered intravenously.

8. The method of claim 1 wherein the protein is insulin.

9. The method of claim 1 wherein the protein is a neuronal growth factor.

10. The method of claim 1 wherein the protein is an immuno-globulin or a monoclonal antibody.

11. The method of claim 10 wherein the immunoglobulin is HIV immune globulin.

12. The method of claim 10 wherein the immunoglobulin or the monoclonal antibody is bound to a second bioactive protein via an antibody-antigen complex.

13. The method of claim 1 wherein the protein is apolipoprotein E.

14. The method of claim 1 wherein the protein is albumin.

15. The method of claim 14 wherein the albumin is complexed with a second bioactive protein.

16. The method of claim 1 wherein the protein is a neuroreceptor.

17. The method of claim 16 wherein the neuroreceptor is complexed to a neuropharmaceutical agent.

18. The method of claim 16 wherein the neuroreceptor is complexed to a neurotransmitter.

* * * * *